(12) United States Patent
Obama

(10) Patent No.: US 12,245,815 B2
(45) Date of Patent: Mar. 11, 2025

(54) OPHTHALMOLOGIC EXAMINATION SYSTEM AND OPHTHALMOLOGIC APPARATUS

(71) Applicant: TOPCON CORPORATION, Tokyo (JP)

(72) Inventor: Tomoya Obama, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 645 days.

(21) Appl. No.: 17/459,434

(22) Filed: Aug. 27, 2021

(65) Prior Publication Data
US 2022/0061661 A1    Mar. 3, 2022

(30) Foreign Application Priority Data

Sep. 2, 2020   (JP) ................................. 2020-147895

(51) Int. Cl.
*A61B 3/16*     (2006.01)
*A61B 3/00*     (2006.01)
(Continued)

(52) U.S. Cl.
CPC .............. *A61B 3/16* (2013.01); *A61B 3/0033* (2013.01); *A61B 3/102* (2013.01); *A61B 3/14* (2013.01); *G16H 10/60* (2018.01); *G16H 40/63* (2018.01)

(58) Field of Classification Search
CPC ... A61B 3/0025; A61B 3/0033; A61B 3/0075; A61B 3/02; A61B 3/022; A61B 3/024;
(Continued)

(56) References Cited

U.S. PATENT DOCUMENTS

2004/0105073 A1    6/2004   Maddalena et al.
2011/0299034 A1   12/2011   Walsh et al.
(Continued)

FOREIGN PATENT DOCUMENTS

CN          1438852      8/2003
CN        209962704      1/2020
(Continued)

OTHER PUBLICATIONS

Extended European Search Report issued Jan. 17, 2022 in corresponding European Patent Application No. 21193972.3.
(Continued)

*Primary Examiner* — Jack Dinh
(74) *Attorney, Agent, or Firm* — Wenderoth, Lind & Ponack, L.L.P.

(57) ABSTRACT

An ophthalmologic examination system that examines a subject's eye with an ophthalmologic apparatus includes an information acquisition portion that acquires a patient's ID determined for each patient and an examination order determined for each patient, an information storage portion that stores the patient's ID and the examination order which are obtained by the information acquisition portion and are linked, an ID reception portion that receives input of the patient's ID, an order read-out portion that reads out the examination order linked to the patient's ID received by the ID reception portion from the information storage portion, and an examination control portion that sets the ophthalmologic apparatus to at least an examination ready state based on the examination order read out by the order read-out portion.

14 Claims, 10 Drawing Sheets

(51) Int. Cl.
*A61B 3/10* (2006.01)
*A61B 3/14* (2006.01)
*G16H 10/60* (2018.01)
*G16H 40/63* (2018.01)

(58) Field of Classification Search
CPC ......... A61B 3/028; A61B 3/032; A61B 3/102; A61B 3/103; A61B 3/107; A61B 3/12; A61B 3/14; A61B 3/15; A61B 3/16; A61B 3/18; G16H 10/60; G16H 40/63
See application file for complete search history.

(56) References Cited

U.S. PATENT DOCUMENTS

| | | | |
|---|---|---|---|
| 2016/0143523 A1 | 5/2016 | Miyashita et al. | |
| 2017/0188816 A1 | 7/2017 | Ono et al. | |
| 2019/0080786 A1 | 3/2019 | Oda | |

FOREIGN PATENT DOCUMENTS

| | | |
|---|---|---|
| DE | 10 2009 004 381 | 7/2009 |
| EP | 3 075 303 | 10/2016 |
| EP | 3 092 941 | 11/2016 |
| EP | 3 222 204 | 9/2017 |
| EP | 3 884 845 | 9/2021 |
| JP | 2004-537331 | 12/2004 |
| JP | 2005-013472 | 1/2005 |
| JP | 2015-112438 | 6/2015 |
| JP | 2015-128482 | 7/2015 |
| JP | 2015-201003 | 11/2015 |
| JP | 2016-073473 | 5/2016 |
| JP | 2016-97251 | 5/2016 |
| JP | 2016-187461 | 11/2016 |
| JP | 2016-209076 | 12/2016 |
| JP | 2018-86304 | 6/2018 |
| JP | 2018-167118 | 11/2018 |
| JP | 2019-49516 | 3/2019 |
| JP | 2019-141642 | 8/2019 |

OTHER PUBLICATIONS

Japanese Office Action issued Mar. 12, 2024 in corresponding Japanese Patent Application No. 2020-147895, with English machine translation.

Office Action issued Jan. 28, 2025 in Japanese Application 2024-107726 (with machine translation thereof).

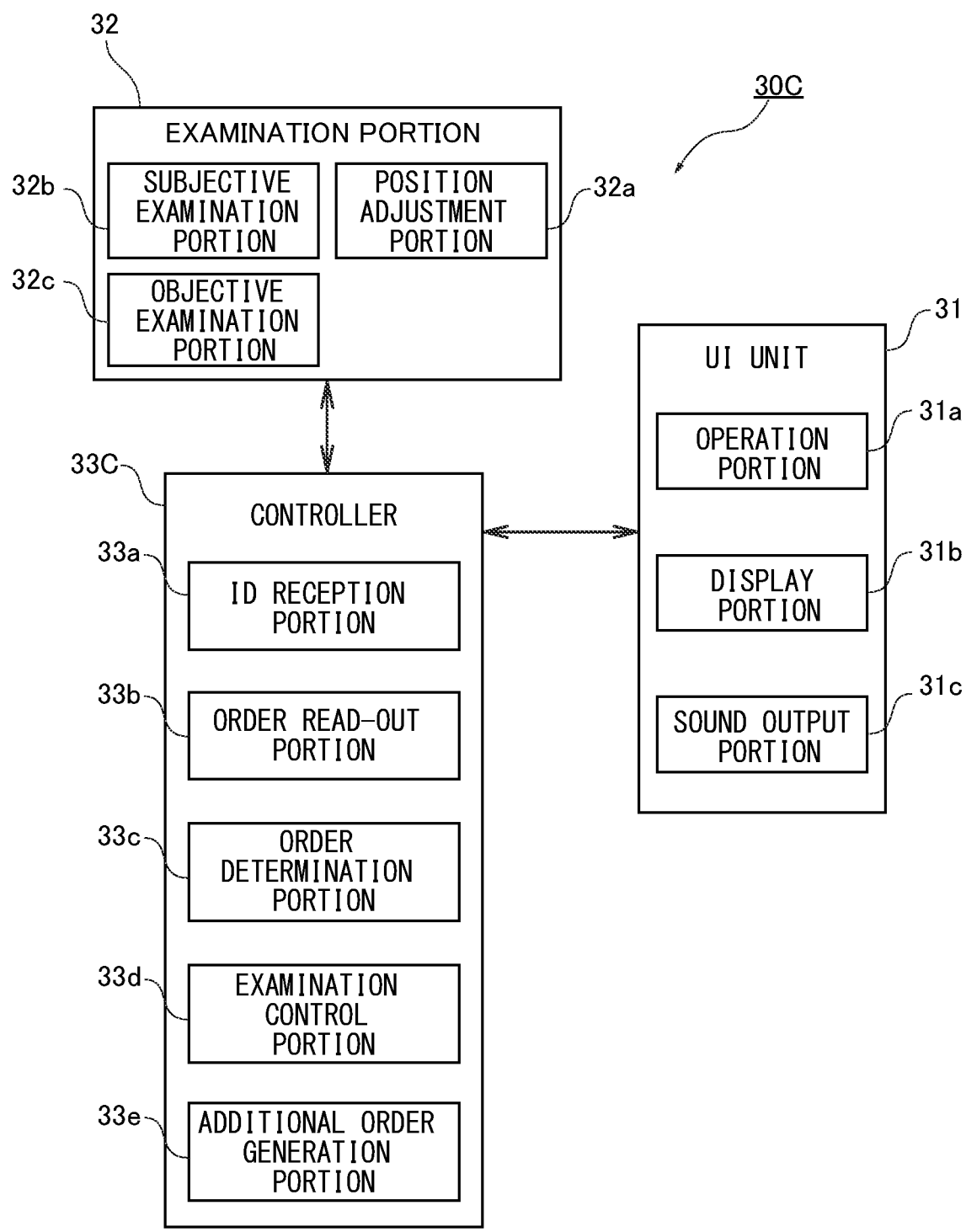

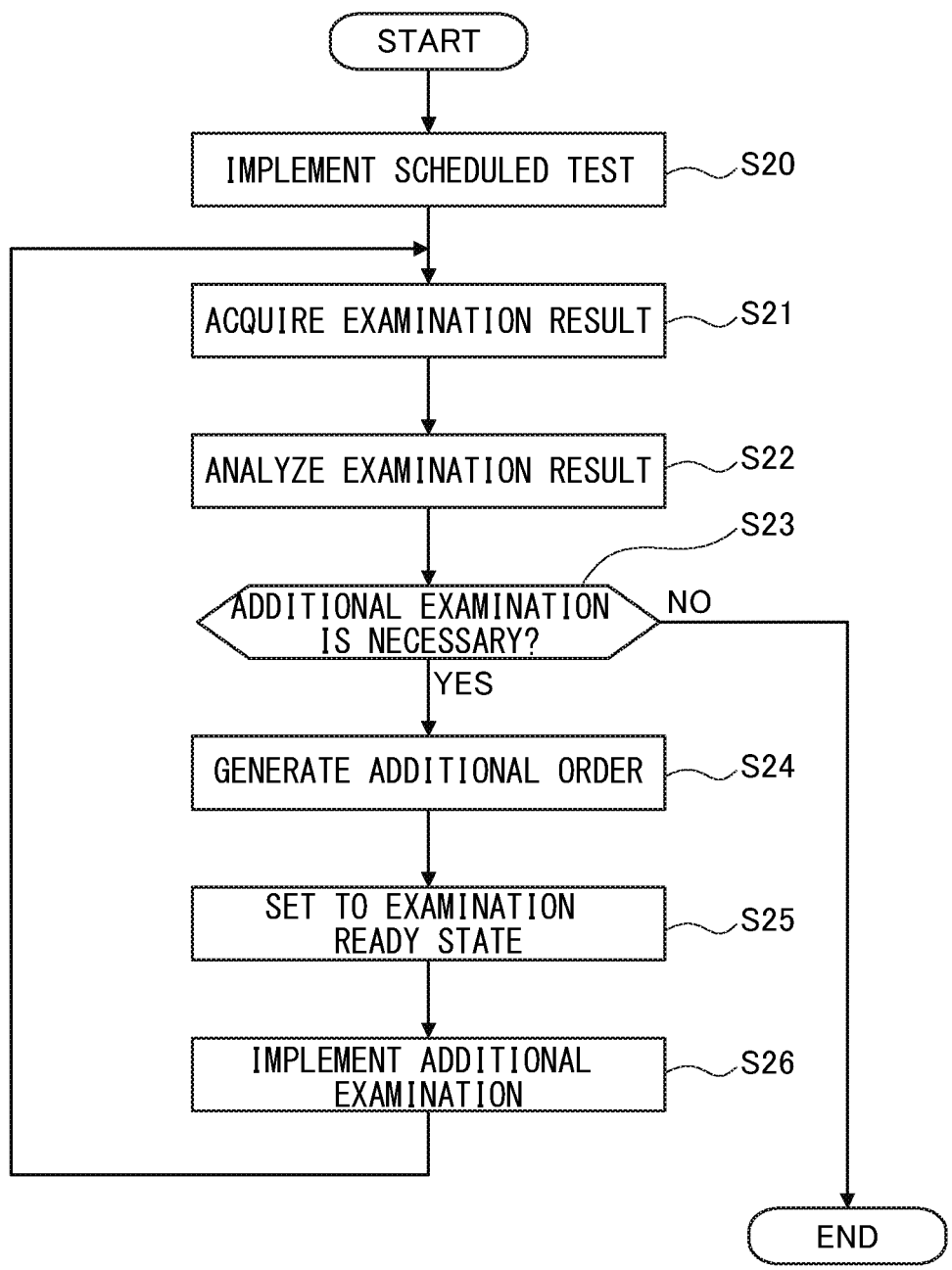

OPHTHALMOLOGIC EXAMINATION SYSTEM AND OPHTHALMOLOGIC APPARATUS

CROSS-REFERENCE TO RELATED APPLICATION

The present application is based on and claims priority from Japanese patent application No. 2020-147895 filed on Sep. 2, 2020, the disclosure of which is hereby incorporated by reference in its entirety.

FIELD OF THE INVENTION

A present disclosure relates to an ophthalmologic examination system and an ophthalmologic apparatus that examine a subject's eye.

BACKGROUND

A complex ophthalmologic apparatus including an intraocular pressure measurement portion that measures intraocular pressure of a subject's eye and an ocular characteristic measurement portion that measures an ocular characteristic except intraocular pressure is conventionally known (see, e.g., JP2015-112438A). An ophthalmologic apparatus capable of photographing a subject's eye in a photographing mode selected from a plurality of photographing modes is also conventionally known (see, e.g., JP2016-97251A).

When a subject's eye is examined with the ophthalmologic apparatus, a necessary examination is implemented based on an examination order predetermined for each patient. At this time, an examiner manually sets the ophthalmologic apparatus after confirming the examination order, and implements the necessary examination. For this reason, the complex ophthalmologic apparatus enabling fundus photographing and tomogram image photographing (OCT photographing) with optical coherence tomography (hereinafter referred to as OCT) may implement an examination different from the examination instructed by the examination order such as the OCT photographing regardless of the examination order of color fundus photographing. The ophthalmologic apparatus may also implement an unnecessary examination that is not instructed by the examination order. Thus, the examination may not be implemented according to the examination order, which makes a problem for the patient due to the implementation of the unnecessary examination and the demand of the unnecessary examination cost.

Therefore, the present disclosure has been made in view of the above circumferences, and an object of the present disclosure is to provide an ophthalmologic examination system and an ophthalmologic apparatus capable of implementing an examination according to an examination order without making a mistake.

SUMMARY

To achieve the above object, an ophthalmologic examination system that examines a subject's eye with an ophthalmologic apparatus according to the present disclosure includes an information acquisition portion that acquires a patient's ID determined for each patient and an examination order determined for the each patient, an information storage portion that stores the patient's ID and the examination order which are obtained by the information acquisition portion and are linked, an ID reception portion that receives input of the patient's ID, an order read-out portion that reads out the examination order linked to the patient's ID received by the ID reception portion from the information storage portion, and an examination control portion that sets the ophthalmologic apparatus to at least an examination ready state based on the examination order read out by the order read-out portion.

To achieve the above object, an ophthalmologic apparatus according to the present disclosure includes an examination portion that examines an ocular characteristic of a patient, an ID reception portion that receives input of a patient's ID determined for each patient, an order read-out portion that reads out an examination order linked to the patient's ID received by the ID reception portion, and an examination control portion that sets the examination portion to an examination ready state based on the examination order read-out by the order read-out portion.

BRIEF DESCRIPTION OF DRAWINGS

FIG. 9 is a block diagram illustrating a configuration of a third modified example of the ophthalmologic apparatus of the first embodiment.

FIG. 10 is a flowchart showing a content of an ophthalmologic examination process that is implemented by the ophthalmologic apparatus of the third modified example.

DETAILED DESCRIPTION

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

Hereinafter, an embodiment of an ophthalmologic apparatus of the present disclosure will be described based on a first embodiment illustrated in the accompanying drawings.

Figure 1:
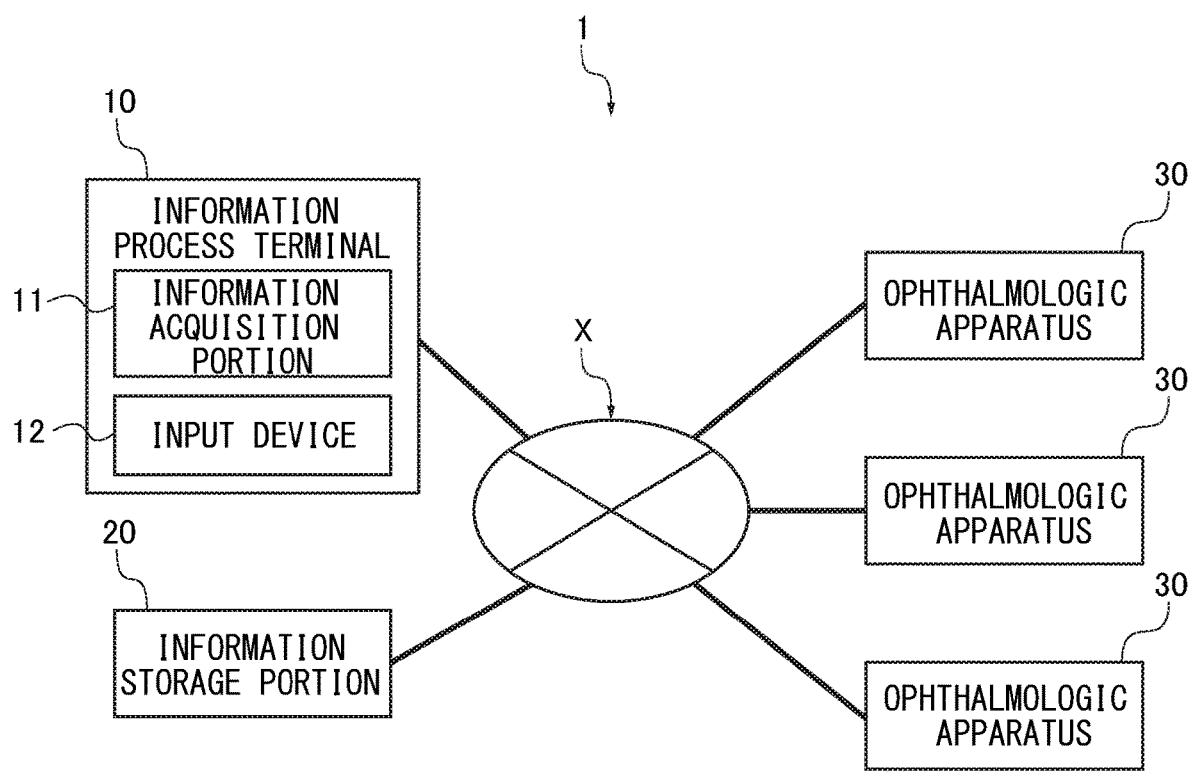
FIG. 1 is a block diagram illustrating a configuration of an ophthalmologic examination system of a first embodiment.

As illustrated in FIG. 1, an ophthalmologic examination system 1 of the first embodiment includes an information process terminal 10, an information storage portion 20, and a plurality of ophthalmologic apparatuses 30. The information process terminal 10, the information storage portion 20, and a plurality of ophthalmologic apparatuses 30 of the ophthalmologic examination system 1 are connected to each other via any communication line X. The communication line X is a wide area network such as the internet and a dedicated line, a local area network such as an in-hospital LAN constituted in a medical institution, a cable connecting a plurality of devices, or a satellite communication network, for example. The communication line X may be a wired communication line or a wireless communication line. The communication line X may be a wired communication line in a part and a wireless communication line in the rest.

The information process terminal 10 may be any computer that is used by a doctor and the like and is installed in a medical institution. The information process terminal 10 includes a hardware such as a processor and a storage device, a software for executing various information processes, and a user interface such as an input device 12 and a display device. The input device 12 may be a keyboard and a mouse. The display device may be a monitor. The information process terminal 10 may be a portable computer (e.g., tablet and laptop computer) or a computer installed in a medical checkup vehicle, for example.

The information process terminal 10 includes an information acquisition portion 11 that acquires a patient's ID determined for each patient and an examination order determined for each patient. In other words, the information acquisition portion 11 acquires the patient's ID and the examination order from information input by a doctor and an operator via the input device 12. Herein, "patient's ID" is meant to be identification information assigned to each patient. The patient's ID may be preset or may be automatically set when inputting information. Herein, "examination order" is meant to be information on an examination that is implemented to a patient and is determined for each patient based on an instruction from the doctor and information on a medical checkup personal history, a disease name, an inquiry result, and an initial diagnosis. The examination order includes information on a patient's ID and an examination implementation date in addition to information on a device for implementing an examination, an examination type, an examination method (scanning pattern), an examination portion or body portion to be examined (e.g., right eye, left eye, and both eyes), an output format (report format), and the like. Note that the information on the patient's ID and the examination order may be shown by a code defined by a predetermined standard.

In the information process terminal 10, when the information acquisition portion 11 acquires the information on the patient's ID and the examination order, the information acquisition portion 11 transmits the acquired information to the information storage portion 20 via the communication line X.

The information storage portion 20 is an electron medium capable of retaining digital data and of reading in (storing) and reading out information. As the examination order includes the information on the patient's ID, the patient's ID and the examination order acquired by the information acquisition portion 11 are linked to be stored in the information storage portion 20. Moreover, as the examination order includes the information on the examination implementation date, the combination of the patient's ID and the examination order is stored in the information storage portion 20 along time series (i.e., in chronological order with other examination orders).

Figure 2:
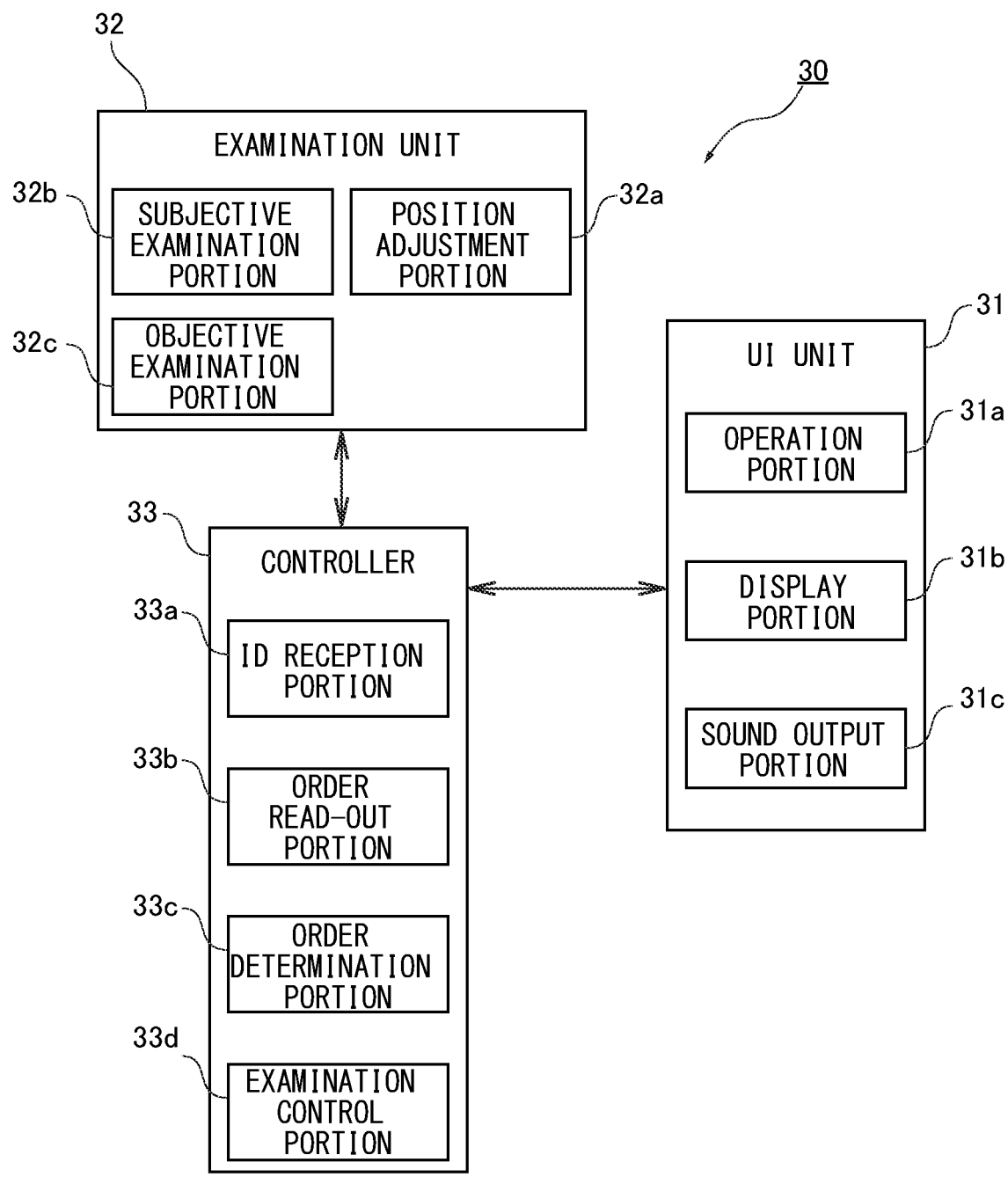
FIG. 2 is a block diagram illustrating a configuration of an ophthalmologic apparatus of the first embodiment.

The ophthalmologic apparatus 30 is an apparatus for use in an examination of a subject's eye of a patient and is installed in a medical institution and a medical checkup vehicle. As illustrated in FIG. 2, the ophthalmologic apparatus 30 includes a user interface unit 31 (hereinafter referred to as UI unit), an examination unit 32, and a controller 33.

The UI unit 31 is used for exchanging information between the ophthalmologic apparatus 30 and a user. The UI unit 31 includes an operation portion 31a, a display portion 31b, and a sound output portion 31c. The operation portion 31a includes an operation lever, a button, a key, a pointing device, a microphone, and a barcode reader. These are operated by the user. For example, the information on the patient's ID is input by this operation portion 31a. The display portion 31b may include a display to display the examination order, the examination result, and the information input via the operation portion 31a. The sound output portion 31c may include a speaker to output the examination result and the result determined by the controller 33 with sound. Note that the information input via the operation portion 31a is input to the controller 33. The information displayed on the display portion 31b and the sound information output via the sound output portion 31c are controlled by a command from the controller 33. A device such as a touch panel display that combines the operation portion 31a and the display portion 31b may be used.

The examination unit 32 includes a plurality of optical systems, and has multi-functions capable of photographing the subject's eye and measuring a plurality of ocular characteristics of the subject's eye simultaneously for both eyes or a single eye. That is, the ophthalmologic apparatus 30 of the first embodiment is a so-called complex machine. The examination unit 32 of the first embodiment includes a position adjustment portion 32a, a subjective examination portion 32b, and an objective examination portion 32c.

The position adjustment portion 32a includes a driving mechanism for aligning the optical systems of the subjective examination portion 32b and the objective examination portion 32c with the subject's eye to drive a driving mechanism by a command from the controller 33 for aligning the optical systems.

The subjective examination portion 32b implements a subjective examination that presents, for example, a target to the patient by the command from the controller 33 and acquires the examination result based on the response of the patient to the target, for example. The subjective examination that can be implemented by the subjective examination portion 32b of the first embodiment includes subjective refraction measurement such as a far-sight examination, a near-sight examination, a contrast examination, and a glare examination and a visual field examination.

The objective examination portion 32c implements the objective examination that irradiates light to the subject's eye by the command from the controller 33 to measure the information (ocular characteristic) on the subject's eye based on the detection result of the return light. This objective examination includes the measurement for acquiring the characteristic of the subject's eye and the photographing for acquiring the image of the subject's eye. In the objective examination portion 32c of the first embodiment, both the measurement of the ocular characteristic and the photographing of the subject's eye can be implemented in multiple ways. The objective examination capable of being implemented by the objective examination portion 32c includes objective refraction measurement (refraction measurement), corneal shape measurement (kerato measurement), intraocular pressure measurement, fundus photographing, OCT photographing, and measurement with OCT.

Figure 3:
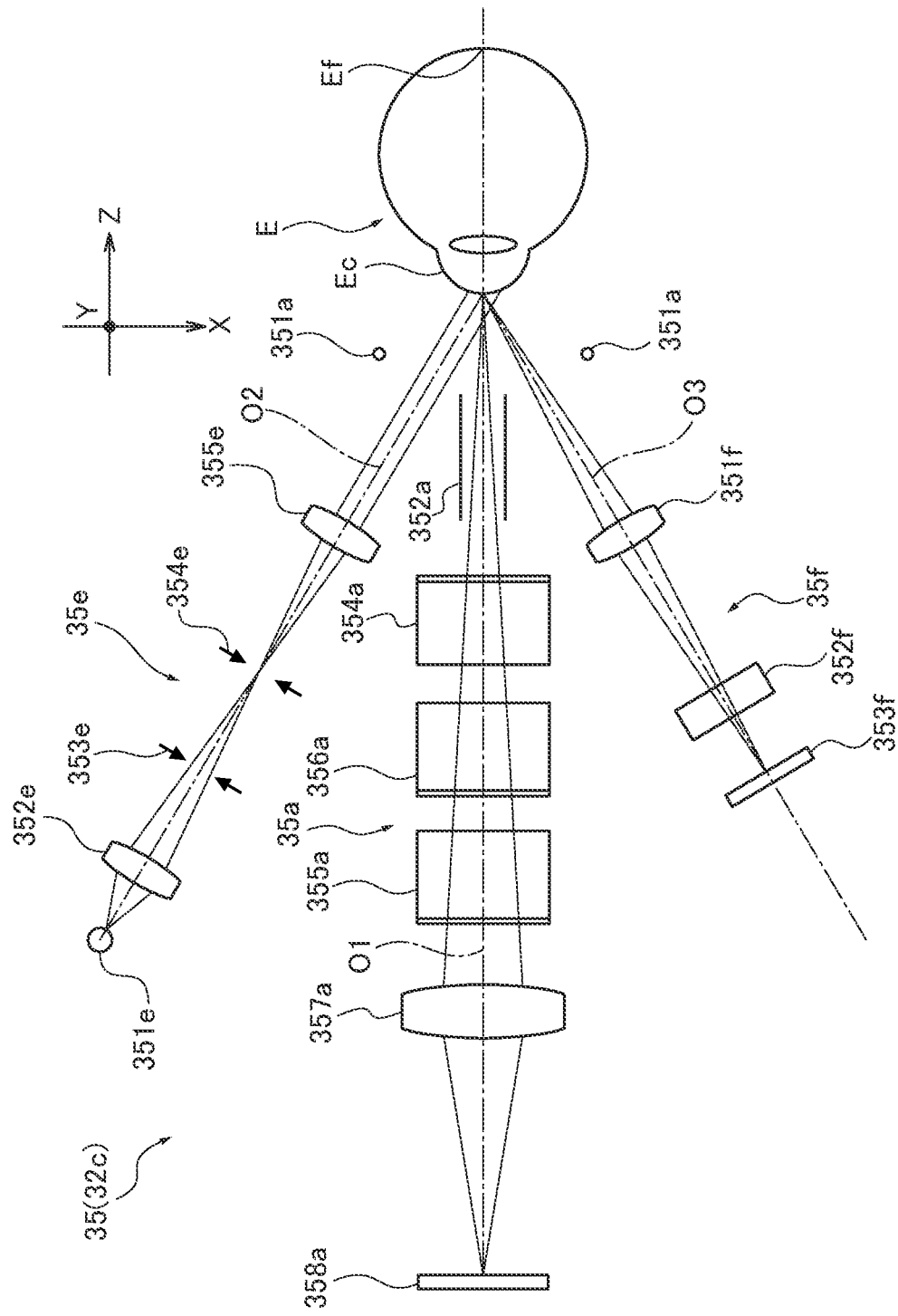
FIG. 3 is a view describing an optical configuration of an intraocular pressure measurement portion of an objective examination portion of the first embodiment.
Figure 4:
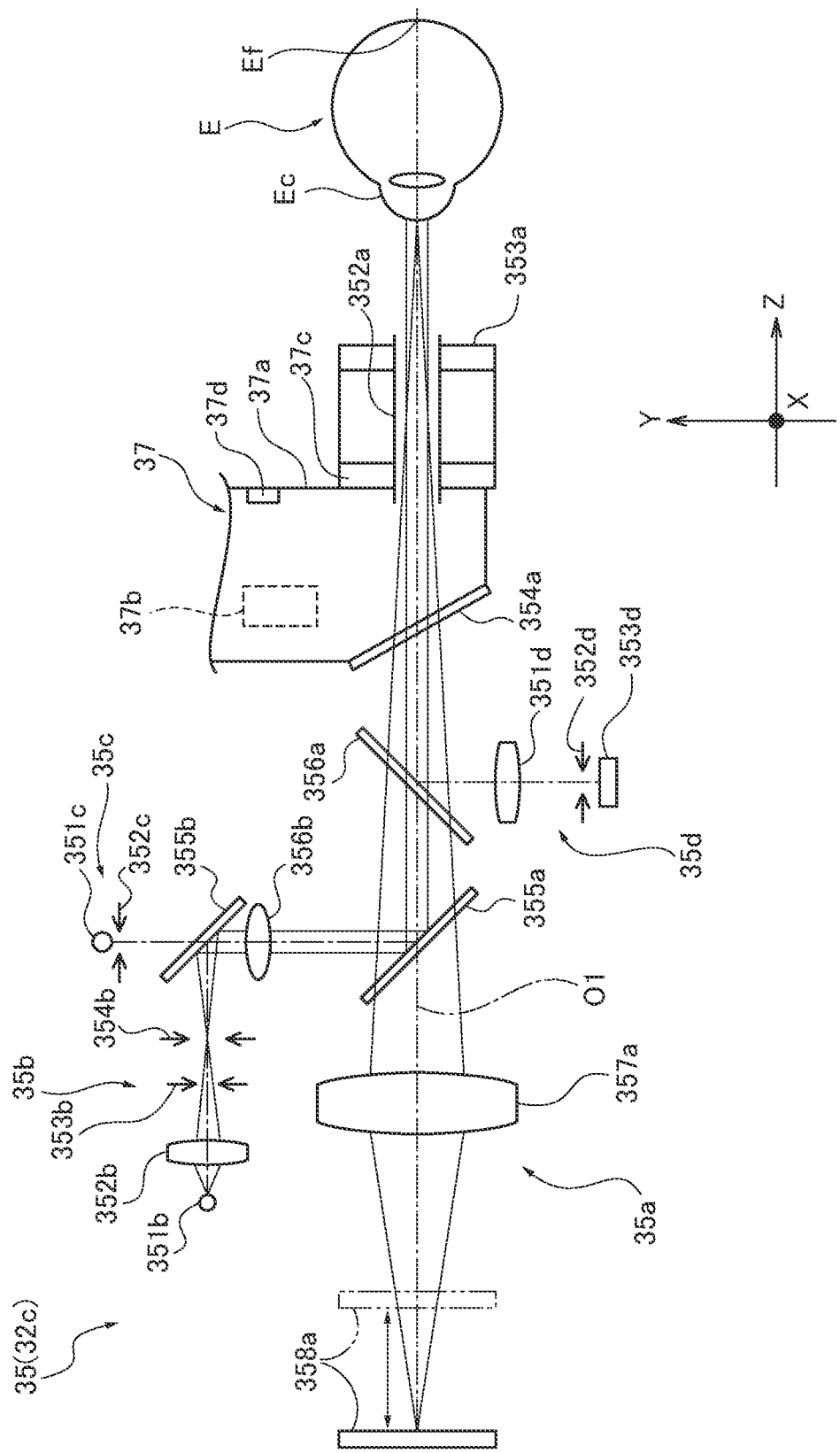
FIG. 4 is a view describing the optical configuration of the intraocular pressure measurement portion of the objective examination portion of the first embodiment as seen from a direction different from FIG. 3.
Figure 5:
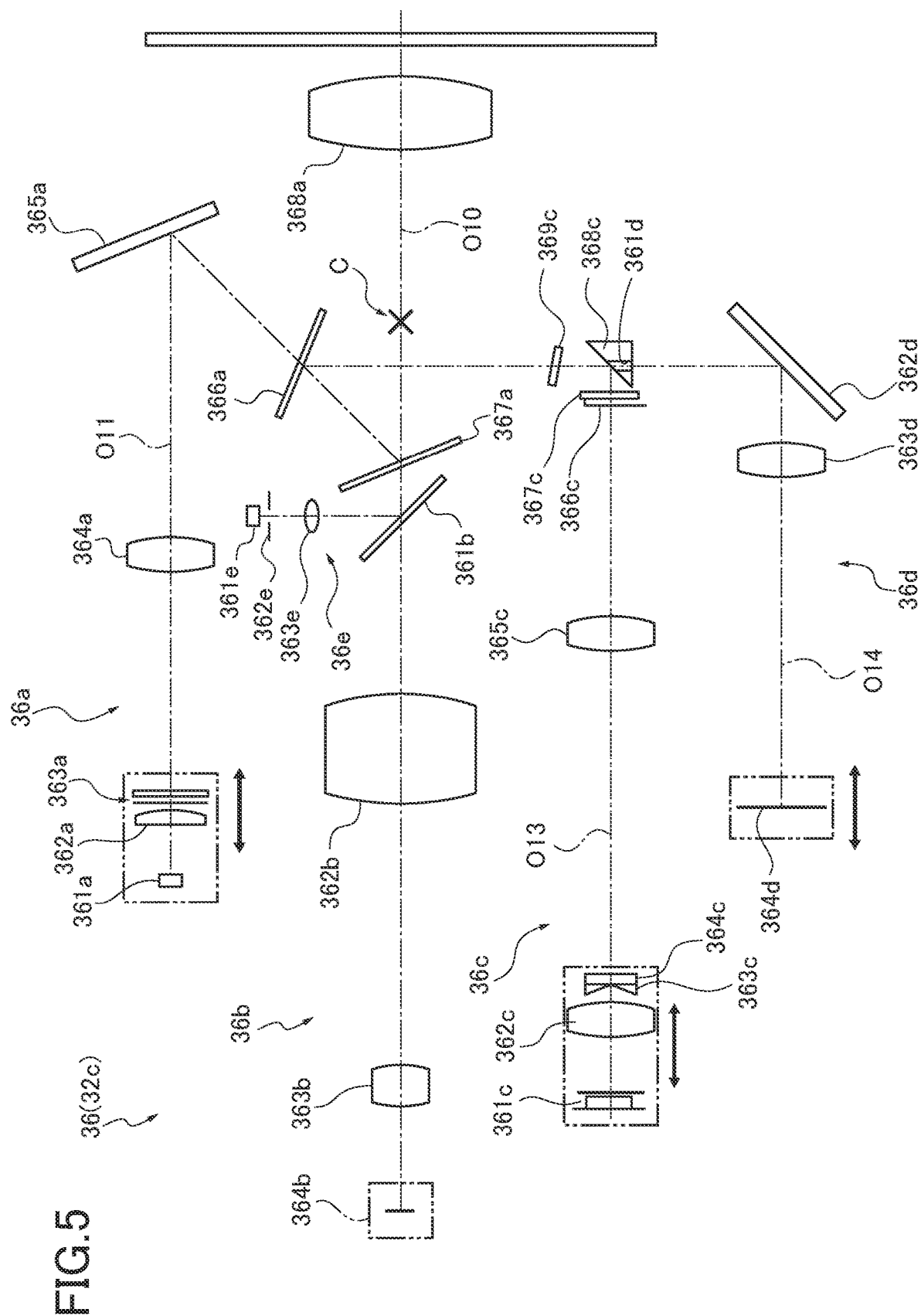
FIG. 5 is a view describing the optical configuration of an ocular characteristic measurement portion of the objective examination portion of the first embodiment.
Figure 6:
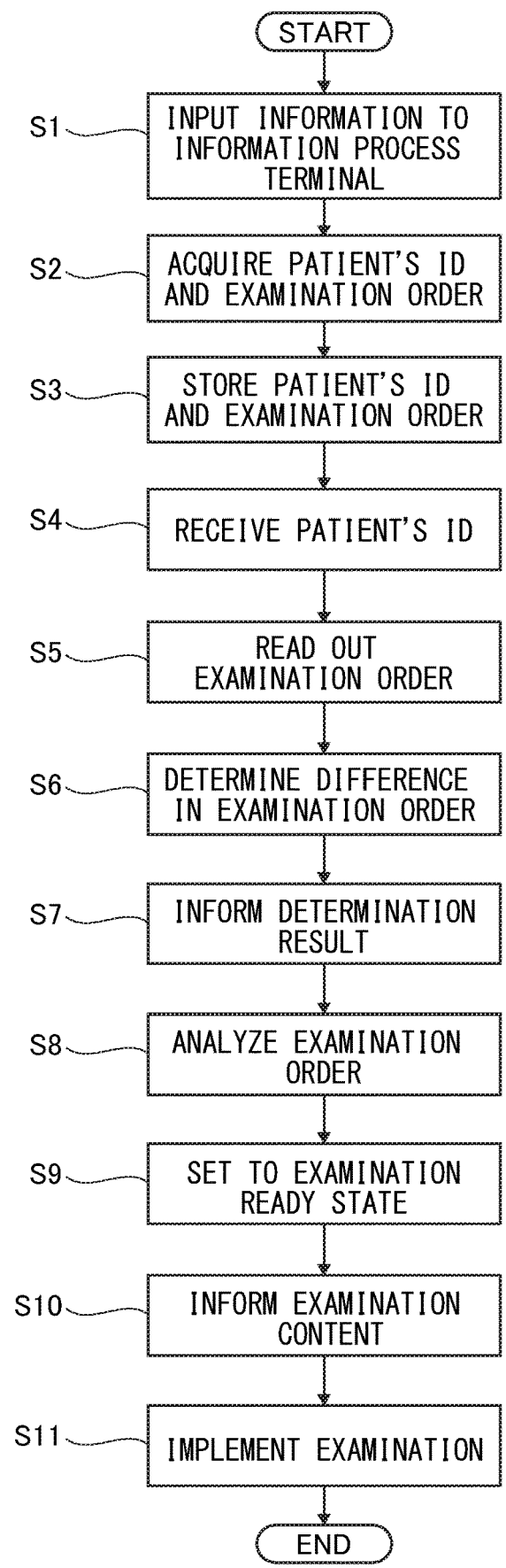
FIG. 6 is a flowchart showing a content of an ophthalmologic examination process that is implemented by the ophthalmologic examination system of the first embodiment.

An example of the detailed configuration of the objective examination portion 32c is illustrated in FIGS. 3 to 5. The objective examination portion 32c illustrated in FIGS. 3 to 5 includes an intraocular pressure measurement portion 35 (see FIGS. 3, 4) that measures an intraocular pressure of a subject's eye E and an ocular characteristic measurement portion 36 (see FIG. 5) that measures an ocular refractive power (e.g., spherical power, cylindrical power, and cylindrical axis angle) of the subject's eye E and the shape of a cornea Ec of the subject's eye E.

The intraocular pressure measurement portion 35 is a non-contact tonometer. As illustrated in FIGS. 3, 4, the intraocular pressure measurement portion 35 includes an anterior ocular segment observation optical system 35a, an XY alignment target projection optical system 35b, a fixation target projection optical system 35c, an applanation detection optical system 35d, a Z alignment target projection optical system 35e, and a Z alignment detection optical system 35f.

The anterior ocular segment observation optical system 35a is used for the observation of the anterior ocular segment of the subject's eye E and the XY alignment (alignment in direction along X-Y plane). The anterior ocular segment observation optical system 35a includes an anterior ocular segment window glass 353a (see FIG. 4) and an anterior ocular segment illumination light source 351a (see FIG. 3) provided around the anterior ocular segment window glass 353a. The anterior ocular segment observation optical system 35a also includes, on an optical axis O1, an air flow blowing nozzle 352a for blowing air flow to the anterior ocular segment of the subject's eye E, the anterior ocular segment window glass 353a, a chamber window glass 354a, a first half mirror 355a, a second half mirror 356a, an objective lens 357a, and a CCD camera 358a. As illustrated in FIG. 4, the CCD camera 358a is movable along the optical axis O1 to be focused on the cornea Ec of the subject's eye E.

The anterior ocular segment observation optical system 35a acquires the anterior ocular segment image of the subject's eye E by the CCD camera 358a while illuminating the subject's eye E with the anterior ocular segment illumination light source 351a. The anterior ocular segment image (light flux of subject's eye E) transmits the anterior ocular segment window glass 353a, the chamber window glass 354a, the second half mirror 356a, and the first half mirror 355a through the outside of the air flow blowing nozzle 352a to be focused by the objective lens 357a and to be formed on a light receiving surface of the CCD camera 358a. The CCD camera 358a generates an image signal based on the image (e.g., anterior ocular segment image) formed on the light receiving surface and outputs the generated image signal to the controller 33.

The XY alignment target projection optical system 35b projects target light to the cornea Ec of the subject's eye E from the front. The target light adjusts the position of the cornea Ec of the subject's eye E as seen in the direction along the X-Y plane (hereinafter referred to as XY direction) to the intraocular pressure measurement portion 35, and enables the alignment in the XY direction. The target light also detects the deformation amount of the cornea Ec of the subject's eye E (degree of deformation (applanation)). This XY alignment target projection optical system 35b includes an XY alignment light source 351b for emitting infrared light, a condenser lens 352b, an aperture stop 353b, a pinhole plate 354b, a dichroic mirror 355b, and a projection lens 356b, and shares the first half mirror 355a with the anterior ocular segment observation optical system 35a.

In the XY alignment target projection optical system 35b, the infrared light emitted from the XY alignment light source 351b pass through the aperture stop 353b while being focused by the condenser lens 352b to travel to a hole portion of the pinhole plate 354b. The light flux passed through the pinhole plate 354b is reflected by the dichroic mirror 355b to travel to the projection lens 356b. The reflected light flux is then converted into parallel light flux by the projection lens 356b to travel to the first half mirror 355a. The parallel light flux of the infrared light is reflected by the first half mirror 355a to travel on the optical axis O1 of the anterior ocular segment observation optical system 35a, and penetrate the second half mirror 356a and the chamber window glass 354a to travel to the inside of the air flow blowing nozzle 352a, and reaches the subject's eye E as the XY alignment target light through the inside of the air flow blowing nozzle 352a.

The fixation target projection optical system 35c projects (present) a fixation target to the subject's eye E. The fixation target projection optical system 35c includes a fixation target light source 351c that emits visible light and a pinhole plate 352c, and shares the dichroic mirror 355b and the projection lens 356b with the XY alignment target projection optical system 35b, and shares the first half mirror 355a with the anterior ocular segment observation optical system 35a.

In the fixation target projection optical system 35c, the fixation target light emitted from the fixation target light source 351c travels to the hole portion of the pinhole plate 352c to pass through the dichroic mirror 355b, and travels to the projection lens 356b. The light flux of the fixation target light is converted into the parallel light by the projection lens 356b, and travels to the first half mirror 355a to be reflected by the first half mirror 355a. The reflected parallel light flux travels on the optical axis O1 of the anterior ocular segment observation optical system 35a. The light flux of the fixation target light passes through the second half mirror 356a and the chamber window glass 354a to travel to the inside of the air flow blowing nozzle 352a, and reaches the subject's eye E through the inside of the air flow blowing nozzle 352a. In the fixation target projection optical system 35c, the patient gazes the fixation target projected to the subject's eye E as the fixation target, so that the visual line of the patient is fixed.

The applanation detection optical system 35d receives the reflection light of the XY alignment target light, which is projected onto the subject's eye E by the XY alignment target projection optical system 35b, by the cornea Ec to detect the deformation amount (applanation) of the surface of the cornea Ec. The applanation detection optical system 35d includes a lens 351d, a pinhole plate 352d, a sensor 353d, and a second half mirror 356a provided on the optical path of the anterior ocular segment observation optical system 35a.

The lens 351d condenses the reflection light of the XY alignment target light by the cornea Ec onto the center hole of the pinhole plate 352c when the surface of the cornea Ec is only flat. The pinhole plate 352d has the center hole to be located in the condensed position by the lens 351d. The sensor 353d is a light receiving sensor capable of detecting light volume to output a signal according to the received light volume. In the applanation detection optical system 35d, the signal according to the light volume received by the sensor 353d is output to the controller 33.

As illustrated in FIG. 3, the Z alignment target projection optical system 35e projects the alignment target light (alignment target parallel light flux) in the Z axis direction at an angle to the cornea Ec of the subject's eye E. The Z alignment target projection optical system 35e includes, on an optical axis O2, a Z alignment light source 351e, the condenser lens 352e, an aperture stop 353e, a pinhole plate 354e, and a projection lens 355e.

In the Z alignment target projection optical system 35e, the infrared light emitted from the Z alignment light source 351e passes through the aperture stop 353e while being condensed by the condenser lens 352e to travel to the pinhole plate 354e. The light flux passed through the hole portion of the pinhole plate 354e travels to the projection lens 355e, and is converted into the parallel light by the projection lens 355e to travel to the cornea Ec. The light flux (Z alignment target light) of the light traveled to the cornea Ec is reflected by the surface of the cornea Ec to form a bright spot image located inside the subject's eye E.

As illustrated in FIG. 3, the Z alignment detection optical system 35f receives the reflection light of the Z alignment target light by the cornea Ec from a direction symmetric to the optical axis O1 of the anterior ocular segment observation optical system 35a to detect the positional relationship between the intraocular pressure measurement portion 35 and the cornea Ec in the Z axis direction. The Z alignment detection optical system 35f includes, on an optical axis O3, an imaging lens 351f, a cylindrical lens 352f, and a sensor 353f. The sensor 353f is a light receiving sensor capable of detecting a light receiving position on a light receiving surface and may be configured with a line sensor or a PSD.

In the Z alignment detection optical system 35f, the reflection light flux of the Z alignment target light reflected by the surface of the cornea Ec is condensed by the cylindrical lens 352f in the Y axis direction while being focused by the imaging lens 351f to form the bright spot image on the sensor 353f. The sensor 353f (Z alignment detection optical system 3M) outputs a signal based on the receiving of the formed bright spot image to the controller 33.

As illustrated in FIG. 4, the air flow blowing mechanism 37 includes an air compression room 37a provided with an air compression driving portion 37b. The air compression driving portion 37b drives under the control of the controller 33 to compress the air inside the air compression room 37a. The air compression room 37a is provided with the air flow blowing nozzle 352a via a transparent glass plate 37c and also the chamber window glass 354a to face the air flow blowing nozzle 352a. The air compression room 37a is provided with a pressure sensor 37d that detects the pressure of the air compression room 37a. This pressure sensor 37d is connected to the controller 33 to output the signal according to the detected pressure to the controller 33.

In the air flow blowing mechanism 37, the air compression driving portion 37b compresses the air inside the air compression room 37a under the control of the controller 33, and blows the air flow to the cornea Ec of the subject's eye E from the air flow blowing nozzle 352a. The air flow blowing mechanism 37 detects the pressure in the air compression room 37a with the pressure sensor 37d to acquire the pressure when blowing the air flow from the air flow blowing nozzle 352a.

In the intraocular pressure measurement portion 35, after the alignment of the intraocular pressure measurement portion 35 is completed with the anterior ocular segment observation optical system 35a, the air flow blowing mechanism 37 is operated to blow the air flow to the cornea Ec of the subject's eye E via the air flow blowing nozzle 352a. The controller 33 acquires the intraocular pressure of the subject's eye E (calculate intraocular pressure value) based on the output from the pressure sensor 37d to display the calculation result on the display portion 31b.

The ocular characteristic measurement portion 36 measures the shape of the cornea Ec of the subject's eye E and the ocular refractive power (e.g., spherical power, cylindrical power, and cylindrical axis angle) of the subject's eye E. As illustrated in FIG. 5, the ocular characteristic measurement portion 36 includes a fixation target projection optical system 36a, an observation optical system 36b, an ocular refractive power measurement ring target projection optical system 36c, a light reception optical system 36d, and an alignment light projection system 36e.

The fixation target projection optical system 36a projects the target to the fundus Ef (see FIGS. 3, 4) of the subject's eye E to fix the vision and fog the subject's eye E. The fixation target projection optical system 36a includes, on an optical axis O11, a fixation target light source 361a, a collimator lens 362a, a target plate 363a provided with a target for fixing and fogging the subject's eye E, a relay lens 364a, a mirror 365a, a first dichroic mirror 366a, a second dichroic mirror 367a, and an objective lens 368a. Herein, the fixation target light source 361a, the collimator lens 362a, and the target plate 363a are integrally movable along the optical axis O11 of the fixation target projection optical system 36a. The second dichroic mirror 367a and the objective lens 368a are arranged on the main optical axis O10 in the ocular characteristic measurement portion 36.

In the fixation target projection optical system 36a, the visible light is emitted from the fixation target light source 361a, and is converted into the parallel light flux by the collimator lens 362a. After that, the parallel light passes through the target plate 363a to be the target light flux. The target light flux is reflected by the mirror 365a after passing through the relay lens 364a, and travels to the second dichroic mirror 367a through the first dichroic mirror 366a. The target light flux traveled to the second dichroic mirror 367a is reflected on the main optical axis O10 in the ocular characteristic measurement portion 36, and travels to the subject's eye E through the objective lens 368a. When the patient grazes the target light flux (fixation target) projected onto the subject's eye E as the fixation target, the fixation target projection optical system 36a fixes the visual line of the patient. The fixation target projection optical system 36a fogs the subject's eye E by moving the fixation target light source 361a and the like from the state in which the patient grazes the fixation target to the unfocused position.

The observation optical system 36b observes the anterior ocular segment (cornea Ec) of the subject's eye E. The observation optical system 36b includes a not-shown illumination light source, and, on the main optical axis O10, a half mirror 361b, a relay lens 362b, an imaging lens 363b, and an imaging element 364b as a secondary fixation imaging element such as a CMOS image sensor. The observation optical system 36b shares the objective lens 368a and the second dichroic mirror 367a with the fixation target projection optical system 36a.

In the observation optical system 36b, the anterior ocular segment (cornea Ec) of the subject's eye E is illuminated by the illumination light flux emitted from the illumination light source. The illumination light flux reflected by the anterior ocular segment passes through the second dichroic mirror 367a and the half mirror 361b via the objective lens 368a to be imaged on the light receiving surface of the imaging element 364b by the imaging lens 363b via the relay lens 362b. The imaging element 364b outputs the image signal based on the acquired image to the controller 33. The controller 33 displays the image of the anterior ocular segment (cornea Ec) on the display portion 31b based on the input image signal.

The ocular refractive power measurement ring target projection optical system 36c projects the pattern light flux as the ocular refractive power measurement ring target to the fundus Ef of the subject's eye E, so as to measure the ocular refractive power of the subject's eye E. The ocular refractive power measurement ring target projection optical system 36c includes an ocular refractive power measurement light source 361c, a lens 362c, a cone prism 363c, a ring target plate 364c, a lens 365c, a bandpass filter 366c, a pupil ring 367c, a holed prism 368c, and a rotary prism 369c. The ocular refractive power measurement ring target projection optical system 36c shares the first dichroic mirror 366a, the second dichroic mirror 367a, and the objective lens 368a with the fixation target projection optical system 36a. The ocular refractive power measurement light source 361c, the lens 362c, the cone prism 363c, and the ring target plate 364c are integrally movable along the optical axis O13 of the ocular refractive power measurement ring target projection optical system 36c.

In the ocular refractive power measurement ring target projection optical system 36c, the light flux emitted from the ocular refractive power measurement light source 361c is converted into the parallel light flux, and the parallel light flux travels to the ring target plate 364c through the cone prism 363c. The light flux passes through the ring pattern portion formed in the ring target plate 364c to be converted into the pattern light flux as the ocular refractive power measurement ring target. The pattern light flux travels to the holed prism 368c via the bandpass filter 366c and the pupil ring 367c, and is reflected by the reflection plane of the holed prism 368c. The reflected pattern light flux travels to the first dichroic mirror 366a via the rotary prism 369c, and is reflected by the second dichroic mirror 367a after being reflected by the first dichroic mirror 366a to travel on the main optical axis O10 in the ocular characteristic measurement portion 36. In the ocular refractive power measurement ring target projection optical system 36c, the pattern light flux is imaged on the fundus Ef of the subject's eye E by the objective lens 368a.

In the light reception optical system 36d, the ocular refractive power measurement ring target image reflected by the fundus Ef of the subject's eye E is received on the imaging element 44d. The light reception optical system 36d includes a hole portion 361d of the holed prism 368c, a mirror 362d, a lens 363d, and an imaging element 364d as a secondary solid imaging element such as a charged coupled device (CCD) image sensor. The light reception optical system 36d shares the objective lens 368a, the second dichroic mirror 367a, and the first dichroic mirror 366a with the fixation target projection optical system 36a, and shares the rotary prism 369c with the ocular refractive power measurement ring target projection optical system 36c. The imaging element 364d is movable along the optical axis O14 of the light reception optical system 36d by the linkage with the ocular refractive power measurement light source 361c and the like of the ocular refractive power measurement ring target projection optical system 36c.

In the light reception optical system 36d, the pattern reflection light flux reflected by the fundus Ef of the subject's eye E (ocular refractive power measurement ring target) is condensed by the objective lens 368a, and is reflected by the first dichroic mirror 366a after being reflected by the second dichroic mirror 367a to travel via the rotary prism 369c. The pattern reflection light flux via the rotary prism 369c passes through the hole portion 361d of the holed prism 368c, and is reflected by the mirror 362d to be imaged on the light receiving surface of the imaging element 364d by the lens 363d. The imaging element 364d outputs the image signal based on the acquired image to the controller 33. The controller 33 displays the image of the ocular refractive power measurement ring target on the display portion 31b based on the input image signal.

The alignment light projection system 36e projects the target light to the subject's eye E to detect the alignment of the ocular characteristic measurement portion 36 in the X-Y direction. The alignment light projection system 36e includes an LED 361e, a pinhole 362e, and a lens 363e. The alignment light projection system 36e shares the half mirror 361b with the observation optical system 36b, and shares the second dichroic mirror 367a and the objective lens 368a with the fixation target projection optical system 36a.

In the alignment light projection system 36e, the light flux from the LED 361e is converted into the alignment target light flux through the hole portion of the pinhole 362e, and the alignment target light flux is reflected by the half mirror 361b via the lens 363e to travel on the main optical axis O10 in the ocular characteristic measurement portion 36. In the alignment light projection system 36e, the alignment target light flux travels to the objective lens 368a via the second dichroic mirror 367a, and is projected as the alignment target light flux toward the cornea Ec of the subject's eye E via the objective lens 368a. In addition, the alignment target light flux is reflected by the cornea Ec of the subject's eye E, and the bright spot image as the alignment target image is projected on the imaging element 364d by the observation optical system 36b. When this bright spot image locates within an alignment mark, the alignment is completed.

In the ocular characteristic measurement portion 36, after the alignment of the ocular characteristic measurement portion 36 is completed with the alignment light projection system 36e, a cornea shape measurement ring target is projected to the cornea Ec from the ocular refractive power measurement ring target projection optical system 36c. The controller 33 measures the spherical power, the cylindrical power, and the axis angle as the ocular refractive power from the image of the anterior ocular segment based on the image signal output from the imaging element 364b with a known method. That is, the controller 33 measures the cornea shape with the ocular characteristic measurement portion 36, also measures the ocular refractive power (optical characteristic), and displays the calculation result and the like on the display portion 31b.

The controller 33 includes a processing circuit such as a central processing unit (CPU) and a storage device (memory), and executes the control and the calculation of each unit (UI unit 31 and examination unit 32) of the ophthalmologic apparatus 30. The controller 33 of the first embodiment includes an ID reception portion 33a, an order read-out portion 33b, an order determination portion 33c, and an examination control portion 33d.

The ID reception portion 33a receives the patient's ID input with the operation portion 31a of the UI unit 31. The patient's ID information received by the ID reception portion 33a is input to the order read-out portion 33b.

The order read-out portion 33b reads out the examination order linked to the patient' ID (hereinafter referred to as "received patient's ID") received by the ID reception portion 33a from the information storage portion 20 based on the patient's ID input from the ID reception portion 33a. The information storage portion 20 stores the combination of the patient's ID and the examination order along time series. Accordingly, the order read-out portion 33b reads out the latest (most recent) examination order and at least one past examination order among the examination orders linked to the received patient's IDs from the information storage portion 20. The latest examination order read out by the order read-out portion 33b is input to the order determination portion 33c and the examination control portion 33d. The past examination order read out by the order read-out portion 33b is input to the order determination portion 33c only.

The order determination portion 33c compares the latest examination order and at least one past examination order based on the examination order input from the order read-out portion 33b to determine a difference in various items such as an examination type and an examination method. After the determination of the difference, the order determination portion 33c outputs an informing command according to the determination result to at least one of the display portion 31b and the sound output portion 31c. As a result, at least one of the display portion 31b and the sound output portion 31c informs the determination result of the order determination portion 33c.

That is, when the order determination portion 33c determines a different item between the latest examination order and the past examination order as "difference", for example, the content of the latest examination order is displayed on the display portion 31b in the black, the item different from the past examination order is displayed on the display portion 31b in the red, and the sound output portion 31c makes the beep sound. When the order determination portion 33c determines the same various items between the latest examination order and the past examination order as "no difference", for example, all items of the latest examination order are displayed on the display portion 13b in the black, and the sound output portion 31c makes the beep sound different from that in the determination of "difference".

That is, the display portion 31b and the sound output portion 31c are the informing portion that informs the determination result of the order determination portion 33c. The determination result of the difference in the examination order may be informed only when "difference" is determined.

The examination control portion 33d outputs a control command that analyzes the latest examination order input from the order read-out portion 33b, and sets the examination unit 32 to be a predetermined examination ready state designated by the examination order based on the analyzed result. Herein, "setting of examination ready state" is meant to set the fundus photographing mode in the objective examination portion 32c after the objective examination portion 32c is aligned to the right eye of the patient by driving the position adjustment portion 32a when the examination order is for the right fundus photographing. That is, "setting of examination ready state" is to set the examination unit 32 to a state just before the implementation of the examination designated by the examination order. In this case, when there are a plurality of photographing modes, the operation portion 31a and the display portion 31b may be limited to prohibit photographing except necessary photographing. When the examination order is shown by a code, the examination order is analyzed by analyzing this code.

In addition, after being set to the examination ready state, when the examiner operates the operation portion 31a and the display portion 31b to input an implementation command, and a predetermined condition such as elapse of a predetermined time is established, the examination unit 32 implements the examination.

Next, the content of the ocular examination process which is implemented by the ophthalmologic examination system 1 of the first embodiment will be described with reference to the flowchart of FIG. 3.

In Step S1, for example, a doctor or an operator inputs necessary information including the patient's ID and the examination order into the information process terminal 10. Then, the process proceeds to Step S2.

In Step S2, following the input of the information into the information process terminal 10 in Step S1, the patient's ID and the examination order are acquired from the information input into the information process terminal 10 by the information acquisition portion 11. Then, the process proceeds to Step S3.

In Step S3, following the acquisition of the patient's ID and the examination order, the acquired patient's ID and the examination order are linked to each other to be stored in the information storage portion 20 along time series. Then, the process proceeds to Step S4.

In Step S4, following the storage of the patient's ID and the examination order, after the patient moves near the ophthalmologic apparatus 30 that implements the examination, the patient's ID is received by the ID reception portion 33a of the ophthalmologic apparatus 30. Then, the process proceeds to Step S5. At this time, the patient's ID is received via the UI unit 31 of the ophthalmologic apparatus 30. More specifically, for example, the examiner selects the patient's ID set to the patient of the examination target from a plurality of patient's IDs displayed on the display portion 31b, reads a barcode described in the clinical record of the patient, and reads the consultation ticket of the patient, so as to receive the information on the input patient's ID.

In Step S5, following the reception of the patient's ID in Step S4, the examination order linked to the received patient's ID (patient's ID received by ID reception portion 33a) is read out from the information storage portion 20 by the order read-out portion 33b. Then, the process proceeds to Step S6. At this time, the order read-out portion 33b reads out the latest examination order and at least one past examination order among the examination orders linked to the received patient's IDs from the information storage portion 20.

In Step S6, following the reading out of the examination order, the difference between the latest examination order and at least one past examination order is determined by the order determination portion 33c. Then, the process proceeds to Step S7.

In Step S7, following the determination of the difference of the examination order in Step S6, the result of the determination by the order determination portion 33c is informed from at least one of the display portion 31b and the sound output portion 31c. Then, the process proceeds to Step S8.

In Step S8, following the informing of the result of the difference determination of the examination order in Step S7, the content of the latest examination order is analyzed by the examination control portion 33d. Then, the process proceeds to Step S9.

In Step S9, following the analysis of the examination order in Step S8, the examination unit 32 of the ophthalmologic apparatus 30 for use in the examination based on the analyzed result is set to the examination ready state by the examination control portion 33d. Then, the process proceeds to Step S10.

In Step S10, following the setting of the examination unit 32 in Step S9, the examination content (which examination is implemented) is informed from at least one of the display portion 31b and the sound output portion 31c. Then, the process proceeds to Step S11. Herein, "informing of examination content" is performed by a screen design, a screen color, and character display of the display portion 31b, and the sound output from the sound output portion 31c. The examination content may be informed by vibrating the operation portion 31a of the UI unit 31. The completion of the setting of the examination unit 32 to the examination ready state can be informed by informing the examination content in the setting completion timing of the examination unit 32.

In Step S11, following the informing of the examination content in Step S10, the examination unit 32 implements the examination to output the result. Then, the process proceeds to the end. At this time, the examination is implemented when the examiner operates the operation portion 31a or after the condition such as the elapse of a predetermined time is established. When a plurality of examinations are implemented, after the implementation of a predetermined examination is completed, the process returns to Step S8, and the steps of the analysis of the examination order, the setting of the examination unit 32, the informing of the examination content, and the implementation of the examination are repeated until a necessary examination is completed.

Next, the operations of the ophthalmologic examination system 1 and the ophthalmologic apparatus 30 of the first embodiment will be described.

When the ocular examination of the patient is implemented in the ophthalmologic examination system 1 of the first embodiment, at first, a doctor or an operator inputs the information including the patient's ID and the examination order of the patient into the information process terminal 10 (Step S1). The information acquisition portion 11 of the information process terminal 10 acquires the examination order and the patient' ID from the input information (Step S2), and links the patient's ID and the examination to be stored in the information storage portion 20 (Step S3).

Next, after the patient moves near the ophthalmologic apparatus 30 that implements the examination, the examiner inputs the patient's ID of the patient with the UI unit 31 of the ophthalmologic apparatus 30 that implements the examination. In the ophthalmologic apparatus 30, the patient's ID is thereby received by the ID reception portion 33a (Step S4), and the examination order linked to the received patient's ID is read out from the information storage portion 20 (Step S5).

Upon the reading out of the examination order, the order determination portion 33c of the ophthalmologic apparatus 30 determines the difference between the latest examination order and the past examination order (Step S6), and informs the determination result from at least one of the display portion 31b and the sound output portion 31c (Step S7).

That is, in the ophthalmologic examination system 1 of the first embodiment, the combination of the patient's ID and the examination order is stored in the information storage portion 20 along time series, and the order read-out portion 33b reads out the latest examination order and at least one past examination order among the examination orders linked to the patient's IDs received by the ID reception portion 33a from the information storage portion 20. The ophthalmologic examination system 1 includes the order determination portion 33c that determines the difference between the latest examination order and the past examination order, and the display portion 31b and the sound output portion 31c (informing portion) that inform the determination result by the order determination portion 33c.

The examiner and the patient can thereby figure out whether or not the latest examination order is different from the past examination order. When the examination order differs, the examiner and the patient can reconfirm the content of the examination order to prevent an examination error and the implementation of an unnecessary examination. It can be proposed to the doctor that the latest examination order differs from the past examination order to review the examination order.

After the determination of the examination order, the examination control portion 33d analyzes the examination order to figure out the examination content (e.g., examination type, examination method (scanning pattern), examination portion (e.g., right eye, left eye, and both eyes), and an output format (report format)) (Step S8). As the examination unit 32 implements the examination according to the examination order, the examination unit 32 is set to the examination ready state (Step S9).

When the examination unit 32 is set to the examination ready state, the examination control portion 33d informs the user (the doctor and/or patient) of the examination content to be implemented by the examination unit 32 via at least one of the display portion 31b and the sound output portion 31c based on the latest examination order read out by the order read-out portion 33b (Step S10). The examiner and the patient can thereby figure out the examination content to be implemented from now on, so that the examination error and the implementation of the unnecessary examination can be controlled.

After that, when the condition such as the operation of the operation portion 31a by the examiner is established, the examination by the examination unit 32 is implemented (Step S11).

As described above, the ophthalmologic examination system 1 of the first embodiment includes the information acquisition portion 11 that acquires the patient's ID determined for each patient and the examination order determined for each patient, the information storage portion 20 that stores the linked patient's ID and examination order which are acquired by the information acquisition portion 11, the ID reception portion 33a that receives the input of the patient's ID, the order read-out portion 33b that reads out the examination order linked to the received patient's ID from the information storage portion 20, and the examination control portion 33d that sets the examination unit 32 of the ophthalmologic apparatus 30 to the examination ready state based on the read out examination order.

The ophthalmologic apparatus 30 of the first embodiment includes the examination unit 32 that examines the ocular characteristic of the patient, the ID reception portion 33a, the order read-out portion 33b, and the examination control portion 33d.

The examination control portion 33d thereby analyzes the examination content designated by the examination order to set the examination unit 32 to a state just before the implementation of the necessary examination. That is, the examiner can automatically set the examination unit 32 to the examination ready state by inputting the patient's ID without manually setting the examination unit 32. As a result, the examination according to the examination order can be reliably implemented while preventing the examination error and the implementation of the unnecessary examination. In particular, as the confusion of the right eye and left eye which often occurs in the ocular examination can be prevented, the patient can effectively receive the necessary examination. By preventing the examination error, an extra time of the examiner and the patient can be controlled, and unnecessary costs spent by the patient and the medical system can be also prevented.

As the confirmation of the examination order by the examiner is unnecessary, the examination can be implemented in a short time while improving the efficiency of the operation. By improving the efficiency of the examination operation, the number of examinations and the number of patients to be examined by one ophthalmologic apparatus 30 can be increased. Such an increase contributes to the depreciation of the apparatus and is effective for the management of the medical institution.

Furthermore, by preventing the examination error, the examination data of the same portion required for a follow-up examination, for example, can be stably acquired. Accordingly, further accurate diagnosis can be made.

In particular, in the first embodiment, the examination unit 32 of the ophthalmologic apparatus 30 has multi-functions that can measure a plurality of ocular characteristics. However, in the ophthalmologic examination system 1 of the first embodiment, the examination control portion 33d analyzes the examination order, and automatically sets the examination unit 32 to the examination ready state. With this configuration, the mode setting error and the examination error can be prevented even when the ophthalmologic apparatus 30 has the multi-functions.

In the ophthalmologic examination system 1 of the first embodiment, a plurality of ophthalmologic apparatuses 30 are connected via the communication line X. With this configuration, when the examination results of a plurality of examinations are acquired, for example, the contradiction of the mutual examination results can be indicated with a function such as an artificial intelligence (AI). Moreover, the examination accuracy (e.g., clear image is photographed and variation when measuring intraocular pressure several times) may be evaluated in addition to the indication of the contradiction of the examination results.

If there is no problem on the examination result, the examination data may be automatically sent to a previously set registration system (e.g., picture archiving and communication systems (PACS), filing system of electronic health record, electronic medical record (EMR), electronic health record (EHR), hospital information system (HIS), and personal health record (PHR)) to register the information. In addition, the examination data may include not only the data of the measurement result but also the report information. After the examiner confirms the examination result, the examination data may be manually sent to a predetermined registration system.

As described above, the ophthalmologic examination system and the ophthalmologic apparatus of the present disclosure are described based on the first embodiment. The specific configurations are not limited to this embodiment, and any change in a design and any addition may be allowed as long as they do not depart from the gist of the invention according to each claim.

In the first embodiment, the controller 33 of the ophthalmologic apparatus 30 includes the ID reception portion 33a, the order read-out portion 33b, and the examination control portion 33d. However, it is not limited thereto. For example, as an ophthalmologic examination system 1A of a first modified example illustrated in FIG. 7, the system may include a management server 40 in addition to the information process terminal 10, the information storage portion 20, and a plurality of ophthalmologic apparatuses 30A. The management server 40 is connected to the information process terminal 10, the information storage portion 20, and a plurality of ophthalmologic apparatus 30A via the communication line X. In the ophthalmologic examination system 1A, each ophthalmologic apparatus 30A includes the UI unit 31 and the examination unit 32. The management server 40 includes the ID reception portion 41, the order read-out portion 42, and the examination control portion 43. The information input via the UI unit 31 of each ophthalmologic apparatus 30A is input to the management server 40 via the communication line X. The UI unit 31 and the examination unit 32 of each ophthalmologic apparatus 30A is separately controlled by the command from the management server 40.

That is, in the ophthalmologic examination system 1A of the first modified example, a plurality of ophthalmologic apparatuses 30A are connected to the examination control portion 43 of the management server 40 through the communication line X. This connection enables the remote control, so that the examination can be implemented without mistaking the examination order even in the ophthalmologic apparatus 30A installed in a remote location without an examiner. The operations of a plurality of ophthalmologic apparatuses 30A can be centrally controlled by the management server 40.

In the ophthalmologic examination system 1A of the first modified example, the examination control portion 43 is connected to a plurality of ophthalmologic apparatuses 30A via the communication line X. The examination control portion 43 selects any one of a plurality of ophthalmologic apparatuses 30A according to the examination order, and sets the selected ophthalmologic apparatus 30A to the examination ready state. Accordingly, the unoccupied ophthalmologic apparatus 30A and the ophthalmologic apparatus 30A most suitable for implementing the examination can be guided to the patient.

Figure 8:
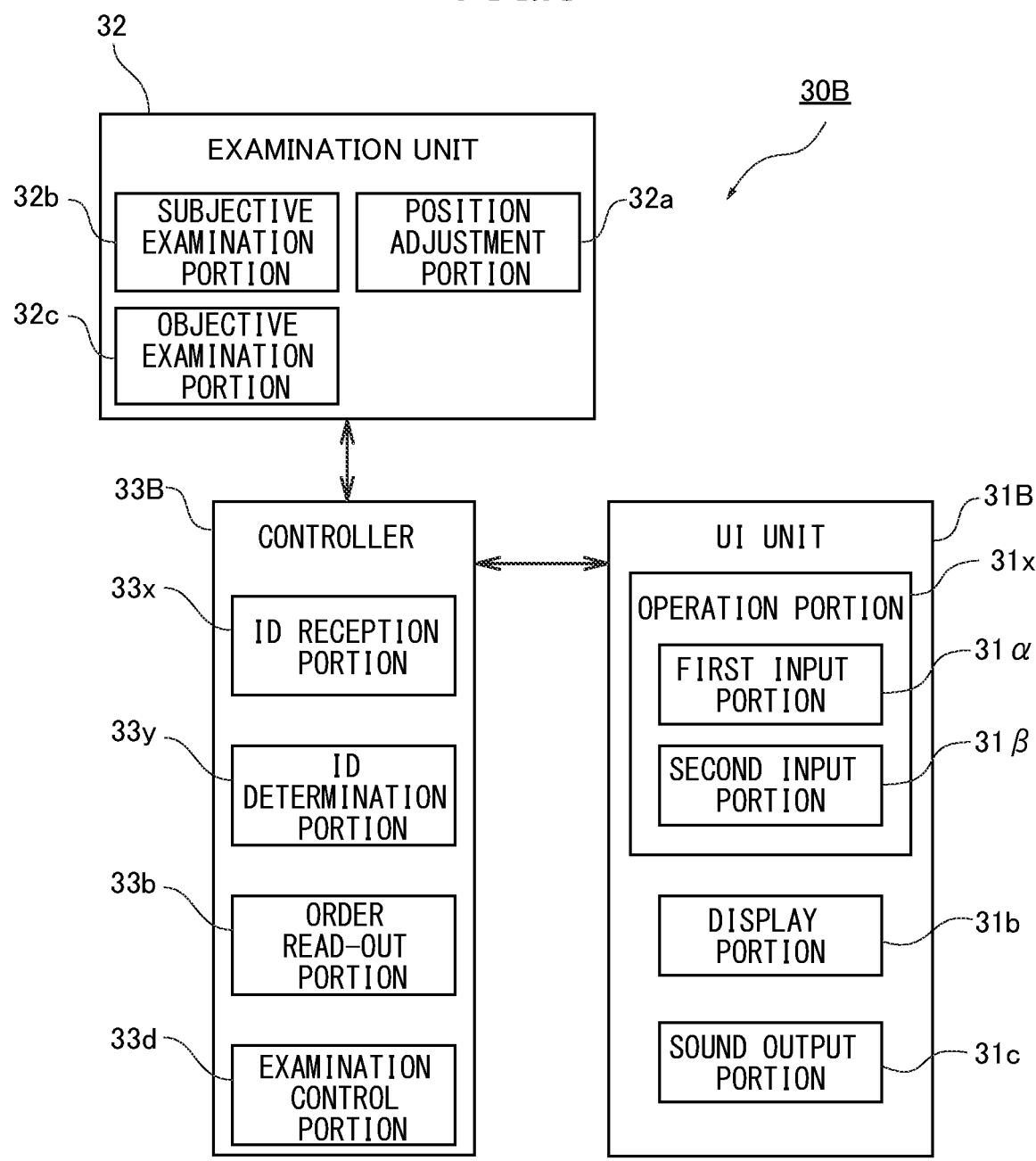
FIG. 8 is a block diagram illustrating a configuration of a second modified example of the ophthalmologic apparatus of the first embodiment.

In the ophthalmologic apparatus 30 of the first embodiment, the patient's ID is input with the operation portion 31a. However, as an ophthalmologic apparatus 30B of a second modified example illustrated in FIG. 8, an operation portion 31x of a UI unit 31B may include a first input portion 31α and a second input portion 31β, and a controller 33B may include an ID reception portion 33x, an ID determination portion 33y, an order read-out portion 33b, and an examination control portion 33d.

The first input portion 31α is a predetermined input device such as a keyboard, and can input the patient's ID. The second input portion 31β is an input device different from the first input portion 31α such as a barcode reader, and can input the patient's ID. The patient's ID (hereinafter referred to as first patient's ID) input with the first input portion 31α is input to the ID reception portion 33x and the ID determination portion 33y. On the other hand, the patient's ID (hereinafter referred to as second patient's ID) input with the second input portion 31β is input to the ID determination portion 33y only.

The ID determination portion 33y compares the patient's ID (first patient's ID) received by the ID reception portion 33x and the patient's ID (second patient ID) determined for the patient who is examined, and determines the coincidence of these IDs. That is, the ID determination portion 33y compares the first patient's ID and the patient's ID (second patient's ID) input with the method different from that of the first patient's ID, and confirms the coincidence of these IDs (i.e., confirms that the IDs correspond).

The examination according to the examination order can be thereby implemented to each patient while preventing the patient from being confused with another patient.

In the ophthalmologic examination system 1 of the first embodiment, the examination is implemented based on the predetermined examination order. However, it is not limited thereto. For example, as an ophthalmologic apparatus 30 of a third embodiment illustrated in FIG. 9, a controller 33C may include an additional order generation portion 33e.

The additional order generation portion 33e acquires the result of the examination (hereinafter referred to as scheduled examination) implemented based on the examination order read out from the information storage portion 20, and generates the examination order (hereinafter referred to as additional order) of the examination which is implemented in addition to the scheduled examination. The additional order generation portion 33e may generate the additional order according to the result of the scheduled examination with the operation of the AI, for example or may generate the additional order predetermined according to the result of the scheduled examination for each patient.

The specific examples of the additional order generated by the additional order generation portion 33e are as follows, for example.

When the result of the scheduled examination is "intraocular pressure value is higher than specified value", an additional order for requesting an optic disc diagnosis by the OCT photographing is generated.

When the result of the scheduled examination is "refractive power is strong negative power value", an additional order for designating the photographing of the fundus image in a wide area is generated in addition to the request of the optic disc diagnosis.

When the result of the scheduled examination is "refractive power shows radical change", an examination order for retesting the refractive power is generated.

An additional order for adding the OCT photographing and the SLO photographing of a targeted portion is generated according to the image diagnosis result of the fundus camera implemented by the scheduled examination.

When the result of the scheduled examination is screening data by a group examination, an additional order for analyzing the result with the AI and implementing a necessary detailed examination is generated.

The additional order generated by the additional order generation portion 33e is input into the examination control portion 33d. The examination control portion 33d analyzes the content of the additional order upon the input of the additional order, and sets the examination unit 32 of the ophthalmologic apparatus 30 for use in the examination to the examination ready state based on the analyzed result. After that, the examination unit 32 set to the examination ready state implements the examination in addition to the scheduled examination.

FIG. 10 shows the flowchart of the ophthalmologic examination process that is implemented by the ophthalmologic apparatus 30C of the third modified example.

In Step S20, the examination (scheduled examination) based on the examination order read out from the information storage portion 20 is implemented by the examination unit 32. Then, the process proceeds to Step S21.

In Step S21, following the implementation of the scheduled examination in Step S20 or the implementation of the additional examination in an after described Step S26, the examination result is acquired by the additional order generation portion 33e. Then, the process proceeds to Step S22.

In Step S22, following the acquisition of the examination result in Step S21, the examination result is analyzed by the additional order generation portion 33e. Then, the process proceeds to Step S23.

In Step S23, following the analysis of the examination result in Step S22, the implementation of the further examination (hereinafter referred to as additional examination) is determined by the additional order generation portion 33e. When it is determined that the implementation of the additional examination is required (YES in Step S23), the process proceeds to Step S24. When it is determined that the implementation of the additional examination is not required (NO in Step S23), a further examination is unnecessary. Then, the process proceeds to the end.

In Step S24, following the determination that the implementation of the additional examination in Step S23 is required, the additional order is generated by the additional order generation portion 33e. Then, the process proceeds to Step S25. The additional order generation portion 33e may generate the generally required additional order with the AI or may generate the additional order according to the result, which is predetermined for each patient.

In Step S25, following the generation of the additional order in Step S24, the content of the additional order is analyzed by the examination control portion 33d, and the examination unit 32 of the ophthalmologic apparatus 30 for use in the additional examination based on the analyzed result is set to the examination ready state. Then, the process proceeds to Step S26.

In step S26, following the setting of the examination unit 32 in Step S25, after informing the content (which additional examination is implemented) of the additional examination, the additional examination is implemented by the examination unit 32 to output the result. Then, the process returns to Step S21.

As described above, the necessity of the implementation of the additional examination can be automatically determined, and the necessary additional order can be automatically generated by the additional order generation portion 33e. A doctor can thereby confirm the result of the scheduled examination, and solve a time for determining the necessity of the implementation of the additional examination and the content of the necessary additional examination, so as to reduce the work load of the doctor. The patient is not required to wait for the diagnosis result by the doctor, and can receive the necessary additional examination following the scheduled examination based on the automatically generated additional order. Accordingly, the time for the patient can be reduced.

Figure 7:
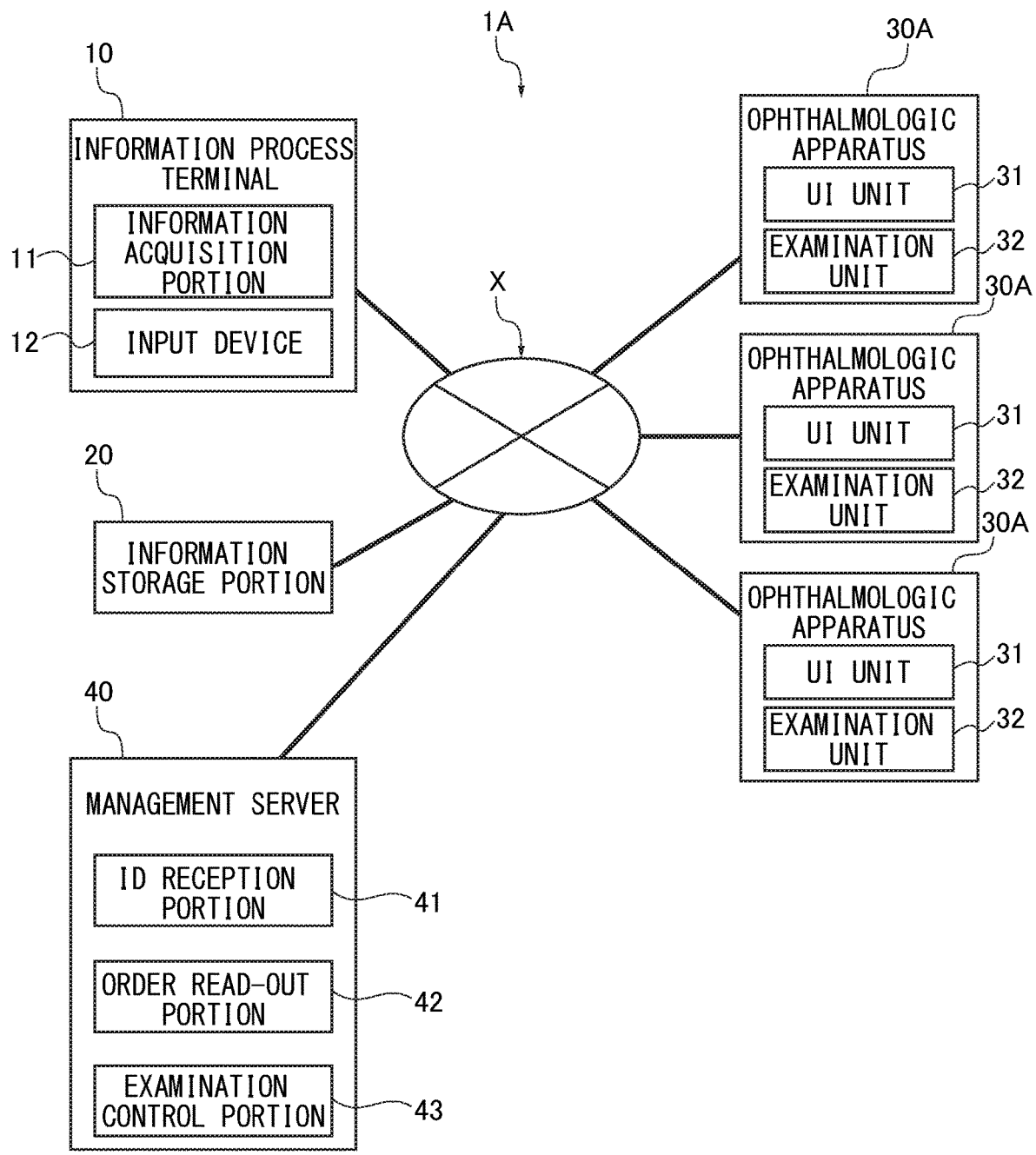
FIG. 7 is a block diagram illustrating a configuration of a first modified example of the ophthalmologic examination system of the first embodiment.

Note that the additional order generation portion 33e may include the management server 40 illustrated in FIG. 7. In this case, the necessary additional order can be generated based on the result of the scheduled examination implemented by a plurality of ophthalmologic apparatuses 30A.

In the ophthalmologic examination system 1 of the first embodiment, the examination unit 32 is set to the examination ready state by the examination control portion 33d, and the examination is implemented when the condition such as the operation of the operation portion 31a by the examiner is established. However, it is not limited thereto. For example, the examination may be controlled until the implementation by the examination control portion 33d based on the examination order read out based on the patient's ID received by the ID reception portion 33a or may be controlled until the output of the examination data that is the result of the implemented examination.

What is claimed is:

1. An ophthalmologic examination system that examines a patient's eye with an ophthalmologic apparatus, the system comprising:

an information acquisition portion configured to acquire the patient's ID determined for the patient and an examination order determined for the patient and linked to the patient's ID, the examination order being information regarding an examination to be implemented on the patient;

an information storage portion configured to store the patient's ID and the examination order obtained by the information acquisition portion;

an ID reception portion configured to receive input of the patient's ID;

an order read-out portion configured to read out the examination order linked to the patient's ID received by the ID reception portion from the information storage portion; and an examination control portion configured to set the ophthalmologic apparatus to an examination ready state based on the examination order read out by the order read-out portion.

2. The ophthalmologic examination system according to claim 1, wherein:

the information storage portion is configured to store a combination of the patient's ID, the examination order being a most recent examination order, and at least one past examination order linked to the patient's ID in chronological order, and the order read-out portion is configured to read out the most recent examination order and the at least one past examination order linked to the patient's ID and received by the ID reception portion, the system further comprising:

an order determination portion configured to determine a difference between the most recent examination order and the at least one past examination order read-out by the order read-out portion; and an informing portion configured to inform a user of a determination result obtained by the order determination portion.

3. The ophthalmologic examination system according to claim 1, wherein the examination control portion is configured to inform a use of an examination content to be implemented by the ophthalmologic apparatus based on the examination order read out by the order read-out portion.

4. The ophthalmologic examination system according to claim 1, wherein the ophthalmologic apparatus is connected to the examination control portion via a communication network.

5. The ophthalmologic examination system according to claim 4, wherein the ophthalmologic apparatus is one of a plurality of ophthalmologic apparatuses, the examination control portion being connected to the plurality of ophthalmologic apparatuses via the communication network, and the examination control portion being configured to select any one of the plurality of ophthalmologic apparatuses according to the examination order to set the selected ophthalmologic apparatus to the examination ready state.

6. The ophthalmologic examination system according to claim 1, further comprising an ID determination portion configured to determine whether the patient's ID received by the ID reception portion corresponds to the patient's ID determined for the patient to be examined.

7. The ophthalmologic examination system according to claim 1, wherein the ophthalmologic apparatus includes multi-functions capable of implementing a plurality of examinations.

8. The ophthalmologic examination system according to claim 1, further comprising an additional order generation portion configured to generate an additional examination order based on a result of an examination of a patient's eye, wherein the examination control portion is configured to set the ophthalmologic apparatus to the examination ready state based on the additional examination order generated by the additional order generation portion.

9. The ophthalmologic examination system according to claim 1, wherein the ID reception portion, the order read-out portion, and the examination control portion are incorporated into a controller comprising a central processing unit and a memory.

10. The ophthalmologic examination system according to claim 1, wherein the examination order includes information regarding at least one of an examination device, an examination type, and a body portion to be examined.

11. An ophthalmologic apparatus comprising:

an examination portion configured to examine an ocular characteristic of a patient;

an ID reception portion configured to receive input of the patient's ID determined for the patient;

an order read-out portion configured to read out an examination order linked to the patient's ID received by the ID reception portion, the examination order being information regarding an examination to be implemented on the patient; and an examination control portion configure to set the examination portion to an examination ready state based on the examination order read-out by the order read-out portion.

12. The ophthalmologic apparatus according to claim 11, wherein the ID reception portion, the order read-out portion, and the examination control portion are incorporated into a controller comprising a central processing unit and a memory.

13. The ophthalmologic apparatus according to claim 11, wherein the examination order is a most recent examination order, the order read-out portion being configured to read out the most recent examination order and at least one past examination order linked to the patient's ID and received by the ID reception portion, the ophthalmologic apparatus further comprising:

an order determination portion configured to determine a difference between the most recent examination order and the at least one past examination order read-out by the order read-out portion; and an informing portion configured to inform a user of a determination result obtained by the order determination portion.

14. The ophthalmologic apparatus according to claim 11, wherein the examination order includes information regarding at least one of an examination device, an examination type, and a body portion to be examined.

* * * * *